(12) United States Patent
Voit et al.

(10) Patent No.: US 6,255,521 B1
(45) Date of Patent: Jul. 3, 2001

(54) METHOD FOR PRODUCING ALIPHATIC ALPHA, OMEGA-AMINO NITRILES

(75) Inventors: Guido Voit, Freinsheim; Andreas Bohnsack, Limburgerhof; Rolf Fischer, Heidelberg; Peter Bassler, Viernheim; Hermann Luyken, Ludwigshafen; Martin Merger, Frankenthal; Klemens Flick, Herxheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/508,965

(22) PCT Filed: Sep. 8, 1998

(86) PCT No.: PCT/EP98/05685

§ 371 Date: Mar. 20, 2000

§ 102(e) Date: Mar. 20, 2000

(87) PCT Pub. No.: WO99/15497

PCT Pub. Date: Apr. 1, 1999

(30) Foreign Application Priority Data

Sep. 24, 1997  (DE) ............................... 197 42 221

(51) Int. Cl.$^7$ ................................ C07C 253/03
(52) U.S. Cl. ............................................. 558/459
(58) Field of Search ............................... 558/459

(56) References Cited

U.S. PATENT DOCUMENTS 3,986,985    10/1976   Dewdney .
4,064,172    12/1977   Dewdney .
5,527,946 *   6/1996   Flick et al. ............................ 558/459

FOREIGN PATENT DOCUMENTS

| 24 29 293  | 3/1975 | (DE) . |
| 44 46 893  | 7/1996 | (DE) . |
| 196 36765  | 3/1998 | (DE) . |
| 223 439    | 5/1987 | (EP) . |
| 98/11059   | 3/1998 | (WO) . |

* cited by examiner

Primary Examiner—Joseph K. McKane
Assistant Examiner—Joseph Murray
(74) Attorney, Agent, or Firm—Keil & Weinkauf

(57) ABSTRACT

The invention relates to a method for producing aliphatic alpha-omega amino nitriles in the presence of a catalyst composed of (a) iron or an iron based compound or a mixture thereof (b) 0.01 to 5 wt. %, in relation to (a), a promoter based on 2, 3, 4, or 5 elements selected from the group comprising aluminum, silicon, zirconium, titanium, and vanadium, and © to 0.5 wt. % in relation to (a) a compound based on an alkaline metal or alkaline-earth metal. The inventive method is characterized in that the aliphatic alpha-omega dinitrile contains 1.0 ppm or more phosphorus. Catalysts are obtainable through the reductive and optional successive passivation of magnetite, whereby the catalysts have a BET surface of 3 to 10 $m^2/g$, a total pore volume of 0.05 to 0.2 ml/g, an average pore diameter of 0.03 to 0.1 mm and a pore volume portion in the range of 0.01 to 0.1 mm of 50 to 70%.

11 Claims, No Drawings

METHOD FOR PRODUCING ALIPHATIC ALPHA, OMEGA-AMINO NITRILES

This application is a 371 of PCT/EP98/05685 filed Sep. 8, 1998.

The present invention relates to a process for the preparation of aliphatic alpha,omega-aminonitriles in the presence of a catalyst, and catalysts which are suitable for the hydrogenation.

DE-A 44 468 93 discloses a process for the preparation of aliphatic alpha,omega-aminonitriles by partial hydrogenation of aliphatic alpha,omega-dinitriles at elevated temperatures and superatmospheric pressure in the presence of a solvent and of a catalyst, by using a catalyst which
(a) contains a compound based on a metal selected from the group consisting of nickel, cobalt, iron, ruthenium and rhodium and
(b) contains from 0.01 to 25, preferably from 0.1 to 5, % by weight, based on (a), of a promoter based on a metal selected from the group consisting of palladium, platinum, iridium, osmium, copper, silver, gold, chromium, molybdenum, tungsten, manganese, rhenium, zinc, cadmium, lead, aluminum, tin, phosphorus, arsenic, antimony, bismuth and rare earth metals, and
(c) from 0 to 5, preferably from 0.1 to 3, % by weight, based on (a), of a compound based on an alkali metal or on an alkaline earth metal,
with the proviso that the component (a) is not based on iron or iron and one of the metals selected from the group consisting of cobalt, ruthenium and rhodium if (b) is a promoter based on a metal selected from the group consisting of titanium, magnesium, chromium and molybdenum, and with the further proviso that, if a compound based on only ruthenium or rhodium or ruthenium and rhodium or nickel and rhodium is chosen as component (a), the promoter (b) can if desired be dispensed with.

The disadvantage of this process is the formation of by-products which are very difficult to separate from the alpha,omega-aminonitriles, such as 6-aminocapronitrile or any further useful products, such as adipodinitrile and hexamethylenediamine in the case of 6-aminocapronitrile as the alpha,omega-aminonitrile.

For example, in the hydrogenation of adipodinitrile to 6-aminocapronitrile and hexamethylenediamine, inter alia 1-amino-2-cyanocyclopentene (ICCP), 2-aminomethylcyclopentylamine (AMCPA), 1,2-diaminocyclohexane (DCH) and bishexamethylenetriamine (BHMTA) are formed in varying amounts.

U.S. Pat. No. 3,696,153 discloses that AMCPA and DCH can be separated from hexamethylenediamine only with very great difficulty.

Furthermore, the time-on-stream of the catalysts in this process is not completely satisfactory.

The prior German patent application 196 36 765.4 describes a process similar to that of the present application, except that, in the process described in 196 36 765.4, the 6-aminocapronitrile (ACN) selectivity is dependent on the age (time-on-stream) of the catalysts used, unless the phosphorus in the adipodinitrile (ADN) used is separated off beforehand. However, separating off phosphorus is technically more difficult and it is desirable to bypass this step.

It is an object of the present invention to provide a process for the preparation of aliphatic alpha,omega-aminonitriles by partial hydrogenation of aliphatic alpha,omega-dinitriles in the presence of a catalyst, which process does not have the stated disadvantages and permits the preparation of alpha, omega-aminonitriles with high selectivity in a technically simple and economic manner, gives long times-on-stream with virtually unchanged conversion and still has a high alpha,omega-aminonitrile selectivity.

We have found that this object is achieved by a process for the preparation of aliphatic alpha,omega-aminonitriles by partial hydrogenation of aliphatic alpha,omega-dinitriles in the presence of a catalyst which
(a) contains iron or a compound based on iron or mixtures thereof and
(b) contains from 0.01 to 5% by weight, based on (a), of a promoter based on 2, 3, 4 or 5 elements selected from the group consisting of aluminum, silicon, zirconium, titanium and vanadium and
(c) from 0 to 0.5% by weight, based on (a), of a compound based on an alkali metal or on an alkaline earth metal, wherein the alpha,omega-dinitrile used contains 1.0 ppm by weight or more of phosphorus.

We have also found catalysts which are obtainable by the reduction and, if required, subsequent passivation of a magnetite, containing
(a) iron or a compound based on iron or mixtures thereof,
(b) from 0.01 to 5% by weight, based on (a), of a promoter based on 2, 3, 4 or 5 elements selected from the group consisting of aluminum, silicon, vanadium, titanium and zirconium, and
(c) from 0 to 0.5% by weight, based on (a), of a compound based on an alkali metal or on an alkaline earth metal,
the catalysts having a BET surface area of from 3 to 10 $m^2/g$, a total pore volume of from 0.05 to 0.2 ml/g, an average pore diameter of from 0.03 to 0.1 $\mu m$ and a pore volume fraction of from 50 to 70% in the range from 0.01 to 0.1 $\mu m$.

Preferred catalyst precursors are those in which the component (a) contains from 90 to 100, preferably from 92 to 99, % by weight, based on (a), of iron oxides, iron hydroxides, iron oxide hydroxides or mixtures thereof. Examples of suitable precursors of this type are iron -(III)-oxide, iron-(II,III)-oxide, iron-(II)-oxide, iron-(II)-hydroxide, iron-(III)-hydroxide and iron oxide hydroxide, such as FeOOH. It is possible to use synthetic or naturally occurring iron oxides, iron hydroxides or iron oxide hydroxides, such as magnetite, which can ideally be described by $Fe_3O_4$, brown hematite, which can be ideally described by $Fe_2O_3 \cdot H_2O$, or red hematite, which can be ideally described by $Fe_2O_3$.

Other preferred catalyst precursors are those in which component (b) contains from 0.01 to 5, preferably from 0.1 to 4, in particular from 0.1 to 2, % by weight of a promoter based on 2, 3, 4 or 5 elements selected from the group consisting of aluminum, zirconium, silicon, titanium and vanadium.

Further preferred catalyst precursors are those in which component (c) contains from 0 to 0.5, preferably from 0.02 to 0.2, % by weight of a compound based on an alkali metal or on an alkaline earth metal, preferably selected from the group consisting of lithium, sodium, potassium, rubidium, cesium, magnesium and calcium.

The novel catalysts may be unsupported or supported catalysts. Examples of suitable carrier materials are porous oxides, such as alumina, silica, aluminosilicates, lanthanum oxide, titanium dioxide, zirconium dioxide, magnesium oxide and zinc oxide, and zeolites and active carbon and mixtures thereof.

The preparation is carried out as a rule by a procedure in which precursors of component (a), if desired together with precursors of promoters components (b) and, if desired, with precursors of the trace components (c), are precipitated in the presence or absence of carrier materials (depending on which catalyst type is desired) and, if desired, the catalyst precursor thus obtained is processed to give extrudates or pellets, dried and then calcined. Supported catalysts are in general also obtainable by impregnating the carrier with a solution of the components (a), (b) and, if desired, (c), it being possible to add the individual components simultaneously or in succession, or by spraying the components (a), if desired (b) and (c) onto the carrier by methods known per se.

Suitable precursors of components (a) are as a rule readily water-soluble salts of iron, such as nitrates, chlorides, acetates, formates and sulfates, preferably nitrates.

Suitable precursors of components (b) are as a rule readily water-soluble salts of complex salts of the above-mentioned metals and semi-metals, such as nitrates, chlorides, acetates, formates and sulfates, preferably nitrates.

Suitable precursors of components (c) are as a rule readily water-soluble salts of the above-mentioned alkali metals and alkaline earth metals, such as hydroxides, carbonates, nitrates, chlorides, acetates, formates and sulfates, preferably hydroxides and carbonates.

The precipitation is effected in general from aqueous solutions, alternatively by adding precipitating reagents, by changing the pH or by changing the temperature.

The catalyst material thus obtained is usually dried, in general at from 80 to 150° C., preferably from 80 to 1200° C.

Calcination is usually carried out at from 150 to 500° C., preferably from 200 to 450° C., in a gas stream comprising air or nitrogen.

After the calcination, the catalyst material obtained is generally exposed to a reducing atmosphere (activation), for example by exposing it at from 200 to 500° C., preferably from 250 to 400° C., for from 2 to 24 hours, to a hydrogen atmosphere or a gas mixture containing hydrogen and an inert gas, such as nitrogen. The catalyst loading here is preferably 200 1 per 1 of catalyst.

Advantageously, the activation of the catalyst is carried out directly in the synthesis reactor since, as a result of this, an intermediate step which is otherwise required, ie. the passivation of the surface at, usually, from 20 to 80° C., preferably from 25 to 35° C., by means of oxygen/nitrogen mixtures, such as air, is usually dispensed with. The activation of passivated catalysts is then preferably carried out in the synthesis reactor at from 180 to 5000° C., preferably from 200 to 350° C., in a hydrogen-containing atmosphere.

The BET surface area of the novel catalysts, determined by $N_2$ adsorption according to DIN 66131, is from 3 to 10 $m^2/g$.

The total pore volume of the novel catalysts, determined by Hg porosimetry according to DIN 66133, is from 0.05 to 0.2 ml/g.

The average pore diameter of the novel catalysts, calculated from the pore volume distribution determined by Hg porosimetry according to DIN 66133, is from 0.03 to 0.1 $\mu$m. The pore volume fraction of the pores having a dimension of from 0.01 to 0.1 $\mu$m of the novel catalysts, read from the pore volume distribution determined by Hg porosimetry according to DIN 66133, is from 50 to 70% by volume.

The catalysts can be used as fixed-bed catalysts in the liquid phase or trickle-bed procedure or as suspended catalysts.

The starting materials used in the novel process are aliphatic alpha,omega-dinitriles of formula I

    I where n is an integer from 1 to 10, in particular 2, 3, 4, 5 or 6. Particularly preferred compounds I are succinonitrile, glutaronitrile, adipodinitrile, pimelonitrile and suberonitrile, very particularly preferably adiponitrile.

The dinitriles of the formula I contain 1.0 ppm by weight or more of phosphorus. Dinitriles whose phosphorus content, determined by atomic emission spectroscopy after acidic digestion of the ADN, is from 1 to 100, preferably from 1 to 20, ppm by weight, based on the dinitrile I or the dinitrile mixture containing dinitriles of the formula I, are suitable. The phosphorus may be present in a variety of forms as a mixture with the dinitrile I or the dinitriles I, for example as organic phosphite or phosphine or the respective decomposition products or secondary products thereof. Dinitriles I which were prepared from alpha,omega-dienes with hydrogen cyanide, as described, for example, in Weissermel, Arpe, Industrielle Organische Chemie, 2nd Edition, pages 233 to 234 (1978), have proven very suitable. Alpha,omega-adiponitrile which is obtainable by an addition reaction of hydrogen cyanide with 1,3-butadiene, for example as described in Weissermel, Arpe, Industrielle Organische Chemie, 2nd Edition, pages 233 to 234 (1978), is particularly suitable.

In the novel process, the dinitriles I described above are partially hydrogenated to alpha,omega-aminonitriles of the formula II

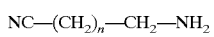    II where n has the above-mentioned meaning, preferably in the presence of a solvent and using a catalyst. Particularly preferred aminonitriles II are those in which n is 2, 3, 4, 5 or 6, in particular 4, ie. 4-aminobutyronitrile, 5-aminopentanenitrile, 6-aminohexanenitrile (6-aminocapronitrile), 7-aminoheptanenitrile and 8-aminooctanenitrile, particularly preferably 6-aminocapronitrile.

If the reaction is carried out in a suspension, temperatures of from 40 to 150° C, preferably from 50 to 100° C., particularly preferably from 60 to 90° C., are usually chosen; the pressure is generally chosen in the range from 2 to 30, preferably from 3 to 30. particularly preferably from 4 to 9, MPa. The residence times are essentially dependent on the desired yield and selectivity and the desired conversion; usually, the residence time is chosen so that a maximum yield is achieved, for example in the range from 50 to 275, preferably from 70 to 200, minutes.

In the suspension procedure, preferably used solvents are ammonia, amines, diamines and triamines of 1 to 6 carbon atoms, such as trimethylamine, triethylamine, tripropylamine and tributylamine, or alcohols, in particular methanol and ethanol, particularly preferably ammonia. Advantageously, a dinitrile concentration of from 10 to 90, preferably from 30 to 80, particularly preferably from 40 to 70, % by weight, based on the sum of the dinitrile and solvent, is chosen.

The amount of catalyst is generally chosen to be from 1 to 50, preferably from 5 to 20, % by weight, based on the amount of dinitrile used.

The suspension hydrogenation can be carried out batchwise or, preferably, continuously, as a rule in the liquid phase.

The partial hydrogenation can also be carried out batchwise or continuously in a fixed-bed reactor by the trickle-bed or liquid phase procedure, usually a temperature of from 20 to 150° C., preferably from 80 to 120° C., and a pressure of, as a rule, from 2 to 40, preferably from 3 to 30, MPa being chosen. The partial hydrogenation is preferably carried out in the presence of a solvent, preferably ammonia, amines, diamines and triamines of 1 to 6 carbon atoms, such as trimethylamine, triethylamine, tripropylamine and tributylamine, or an alcohol, preferably methanol and ethanol, particularly preferably ammonia. In a preferred embodiment, an ammonia content of from 1 to 10, preferably from 2 to 6, g per g of adiponitrile is chosen. A catalyst space velocity of from 0.1 to 2.0, preferably from 0.3 to 1.0, kg of adiponitrile/1*h is preferably chosen. Here too, the conversion and hence the selectivity can be controlled by changing the residence time.

The partial hydrogenation can be carried out in a conventional reactor suitable for this purpose.

In the hydrogenation, a mixture which contains 6-aminocapronitrile, hexamethylenediamine and adipodinitrile is obtained.

6-aminocapronitrile, hexamethylenediamine and a fraction containing essentially adiponitrile can be separated from the mixture in a manner known per se, preferably by distillation, for example according to DE-A 195 002 22 or German application 19 548 289.1, simultaneously or in succession.

The adiponitrile obtained by the novel process can be used again for the partial hydrogenation to hexamethylenediamine and 6-aminocapronitrile, acidic treatment of the ACN to be recycled being carried out to avoid an increase in the level of by-products which prevent on-spec preparation of hexamethylenediamine and/or 6-aminocapronitrile and/or adversely affect the time-on-stream of the catalyst for the partial hydrogenation.

The novel process gives alpha,omega-aminonitriles in good selectivities. Furthermore, the catalysts used according to the invention have a substantially longer time-on-stream in combination with high ACN selectivity, than comparable prior art catalysts. The alpha,omega-aminonitriles are important starting compounds for the preparation of cyclic lactams, in particular 6-aminocapronitrile for caprolactam. In the examples:

| ADN | is | adipodintrile |
| ACN | is | 6-aminocapronitrile |
| HMD | is | hexamethylenediamine |
| DCH | is | cis + trans-1,2-diaminocyclohexane |
| AMCPA | is | 1-amino-2-aminomethylcyclopentane |

EXAMPLE 1 a) Catalyst preparation

The catalyst was prepared by heating a magnetite ore for six hours at 150° C. under nitrogen. The magnetite ore used had the following composition: 72% by weight of Fe, 0.07% by weight of Al, 0.03% by weight of Ca, 0.04% by weight of Mg, 0.11% by weight of Si and 0.01% by weight of Ti, the remainder being oxygen. The sum of the promoters from group b) is 0.19% by weight and the sum of the promoters from group c), calculated as oxides, is 0.11% by weight.

The cooled melt block was comminuted in a jaw crusher, and a sieve fraction having a particle size of from 3 to 6 mm was separated off by sieving. The oxidic catalyst was reduced in an $H_2/N_2$ stream at 450° C. for 72 hours. After cooling to room temperature under nitrogen, the Fe catalyst was passivated with an $N_2$/air stream (for 24 hours with 1% of air in nitrogen), it being ensured that the temperature in the catalyst bed did not increase above 450° C.

(b) Partial hydrogenation of ADN to ACN.

A tube reactor (length 180 cm, d=30 mm) was filled with 740 ml (1,819 g) of the catalyst material prepared according to (a) and reduced at atmospheric pressure in a hydrogen stream (500 1 (S.T.P.)/h). The temperature was increased from 30° C. to 340° C. in the course of 24 hours and then kept at 340° C. for 72 hours.

After the temperature had decreased, a mixture of 400 ml/h of ADN which was prepared from 1,3-butadiene and hydrogen cyanide (HCN) and had a phosphorus content of 4 ppm by weight, 660 ml/h of ammonia and 500 1 (S.T.P.)/h of hydrogen was fed to the reactor at 250 bar.

After a running time of 2,000 hours at a reaction temperature of 120° C., the ACN selectivity had decreased only insignificantly from 50% to 48% with a constant conversion and constant total selectivity (ACN+HMD) of 99% over the total running time.

The content of DCH in the discharged hydrogenation mixture was 2,000 ppm by weight, based on HMD.

The content of AMCPA in the discharged hydrogenation mixture was 50 ppm by weight, based on HMD.

Comparative Example a) Catalyst preparation

Heating a mixture of magnetite, potassium carbonate, $Al_2O_3$ and calcium carbonate, crushing the solidified melt and sieving according to A. B. Stiles, T. A. Koch, Catalyst Manufacture (1995), pages 167/168, gave an oxidic material of the following composition: 1.1% by weight of $K_2O$, 3.0% by weight of $Al_2O_3$, 2.3% by weight of CaO, 0.11% by weight of Si, 0.01% by weight of Ti, remainder Fe oxides.

This material was then reduced in an $N_2/H_2$ stream at 450° C. for 72 hours, passivated with an $N_2$/air mixture (for 24 hours with 1% of air in nitrogen) at room temperature, the temperature in the catalyst bed not increasing above 45° C., and washed with water for 7 days.

The catalyst material obtained had the following composition: 1.2% by weight of Al, 0.74% by weight of Ca, 0.02% by weight of K, 0.11% by weight of Si, 0.01% by weight of Ti, remainder Fe/Fe oxide. The sum of the promoters from group b) is 1.32% by weight, and the sum of the promoters from group c), calculated as oxides, is 1.06% by weight.

b) Partial hydrogenation of ADN to ACN

A tube reactor (length 180 cm, d=30 mm) was filled with 740 ml (1819 g) of the catalyst material prepared according to (a) and reduced at atmospheric pressure in a hydrogen stream (500 1 (S.T.P.)/h). The temperature was increased from 30° C to 340° C in the course of 24 hours and then kept at 340° C. for 72 hours.

After the temperature had decreased, a mixture of 400 ml/h of ADN, which was prepared from 1,3-butadiene and hydrogen cyanide (HCN) and had a phosphorus content of 4 ppm by weight, 660 ml/h of ammonia and 500 l (S.T.P.)/h of hydrogen was fed to the reactor at 250 bar.

After a running time of 2000 hours at a reaction temperature of 120° C., the ACN selectivity had decreased from 40% to 25% with a constant conversion and constant total selectivity (ACN+HMD) of 99% over the total running time.

The content of DCH in the discharged hydrogenation mixture was 4,000 ppm by weight, based on HMD.

The content of AMCPA in the discharged hydrogenation mixture was 150 ppm by weight, based on HMD.

We claim:

1. A process for the preparation of aliphatic alpha, omega-aminonitriles by partial hydrogenation of aliphatic alpha, omega-dinitriles in the presence of a catalyst which (a) contains iron or a compound based on iron or mixtures thereof and (b) contains from 0.01 to 5% by weight, based on (a), of a promoter based on 2, 3, 4 or 5 elements selected from the group consisting of aluminum, silicon, zirconium, titanium and vanadium and (c) from 0 to 0.5% by weight, based on (a), of a compound based on an alkali metal or on an alkaline earth metal, wherein the alpha,omega-dinitrile used contains 1.0 ppm by weight or more of phosphorus.

2. The process as claimed in claim 1, wherein the catalyst is obtainable by reduction and, if required, subsequent passivation of a magnetite and has a BET surface area of from 3 to 10 m$^2$/g, a total pore volume of from 0.05 to 0.2 ml/g, an average pore diameter of from 0.03 to 0.1 µm and a pore volume fraction of from 50 to 70% in the range from 0.01 to 0.1 µm.

3. The process as claimed in claim 1, wherein an iron oxide or a mixture of iron oxides is used as the compound based on iron.

4. The process as claimed claim 1, wherein a promoter based on aluminum, silicon and vanadium is used.

5. The process as claimed in claim 1, wherein the catalyst is a supported catalyst.

6. The process as claimed claim 1, wherein the catalyst is an unsupported catalyst.

7. The process as claimed claim 1, wherein the dinitrile used is adiponitrile, 6-aminocapronitrile being obtained.

8. The process as claimed claim 1 for the simultaneous preparation of 6-aminocapronitrile and hexamethylenediamine starting from adiponitrile by (1) partial hydrogenation of adiponitrile in the presence of a catalyst, a mixture containing 6-aminocapronitrile, hexamethylenediamine and adiponitrile being obtained, and (2) isolation of 6-aminocapronitrile and hexamethylenediamine from the mixture.

9. The process as claimed claim 1, wherein the hydrogenation is carried out in a suspension.

10. The process as claimed claim 1, wherein the hydrogenation is carried out in a fixed-bed reactor.

11. The process as claimed claim 1, wherein the alpha, omega-dinitrile used was obtained by hydrocyanation - in the presence of phosphorus-containing catalysts—of an alpha,omega-diene having two fewer carbon atoms.

* * * * *

UNITED STATES PATENT AND TRADEMARK OFFICE
CERTIFICATE OF CORRECTION

PATENT NO. : 6,255,521 B1  Page 1 of 1
DATED : July 3, 2001
INVENTOR(S) : Voit et al.

It is certified that error appears in the above-identified patent and that said Letters Patent is hereby corrected as shown below:

<u>Title page,</u>
ABSTRACT,
Line 7, "©" should read -- (c) from 0 --;
Line 8, "alkaline" should be -- alkali --.

At the following places, "claimed claim" should be -- claimed in --:
<u>Column 7,</u> claim 4, line 15;
        claim 5, line 17;
        claim 6, line 19;
        claim 7, line 21;

<u>Column 8,</u> claim 8, line 1;
        claim 9, line 12;
        claim 10, line 14;
        claim 11, line 16.

Signed and Sealed this

Twenty-second Day of January, 2002

Attest:

*Attesting Officer*

JAMES E. ROGAN
*Director of the United States Patent and Trademark Office*